United States Patent [19]

Zimmerman et al.

[11] Patent Number: 5,374,623
[45] Date of Patent: Dec. 20, 1994

[54] CYSTEINE PROTEASE INHIBITORS EFFECTIVE FOR IN VIVO USE

[75] Inventors: Mary P. Zimmerman, Pleasanton; Eugene R. Bissell, Alamo; Robert E. Smith, Livermore, all of Calif.

[73] Assignee: Prototek, Inc., Dublin, Calif.

[21] Appl. No.: 932,791

[22] Filed: Aug. 20, 1992

[51] Int. Cl.$^5$ .................. A61K 37/02; C07K 5/06; C07K 5/08; C07K 5/10
[52] U.S. Cl. .................. 514/17; 530/330; 530/332; 530/331; 544/168; 560/10; 560/18; 560/37; 560/45
[58] Field of Search ............ 530/330, 331, 332; 514/17, 18, 19; 560/10, 18, 37, 45; 544/168, 122

[56] References Cited

U.S. PATENT DOCUMENTS 4,518,528  5/1985  Rasnick .................. 260/112.5 R
5,055,451  10/1991  Krantz et al. ................ 514/19

FOREIGN PATENT DOCUMENTS 0272671  6/1988  European Pat. Off. ........... 514/19

OTHER PUBLICATIONS van Noorden and Everts, "Selective Inhibition of Cysteine Proteinases by Z-Phe-AlaCH$_2$F Suppresses Digestion of Collagen by Fibroblasts and Osteoclasts," 178 *Biochemical and Biophysical Research Communications* 178–184 (1991).

Rifkin, Vernillo, Kleekner, Auszmann, Rosenberg and Zimmerman, "Cathepsin B and L Activities in Isolated Osteoclasts," 179 *Biochemical and Biophysical Research Communications* 63–69 (1991).

Grinde, "The Thiol Proteinase Inhibitors, Z-Phe-Phe-CHN$_2$ and Z-Phe-Ala-CHN$_2$, Inhibit Lysosomal Protein Degradation in Isolated Rat Hepatocytes," 757 *Biochimica et Biophysica Acta* 15–19 (1983).

Mason, Bartholomew and Hardwick, "The Use of Benzyloxycarbonyl[$^{125}$I]iodotyrosylalanyldiazomethane as a Probe for Active Cysteine Proteinases in Human Tissues," 263 *Biochem. J.* 945–949 (1989).

van Noorden, Smith and Rasnick, "Cysteine Proteinase Activity in Arthritic Rat Knee Joints and the Effects of a Selective Systemic Inhibitor, Z-Phe-Ala-CH$_2$F," 15 *J. Rheumatol.* 1525–1535 (1988).

(List continued on next page.)

*Primary Examiner*—Floyd D. Higel
*Attorney, Agent, or Firm*—Woodard, Emhardt, Naughton Moriarty & McNett

[57] ABSTRACT

A method of treating medical conditions with proteinase inhibitors of the formula:

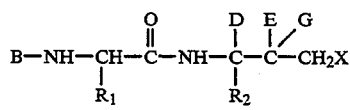

wherein

B is H or an amino acid blocking group for the N-terminal amino acid nitrogen;

R$_1$ is an optionally protected α-amino acid side chain such that P$_2$ is the residue of an α-amino acid selected from the group consisting of phenylalanine (Phe), leucine (Leu), tyrosine (Tyr) and valine (Val), and substituted analogs thereof, particularly including Tyr(OMe);

R$_2$ is an optionally protected α-amino acid side chain such that P$_1$ is the residue of an α-amino acid selected from the group consisting of alanine (Ala), arginine (Arg), aspartic acid (Asp), glutamic acid (Glu), histidine (His), homophenylalanine (HPhe), phenylalanine (Phe), ornithine (Orn), serine (Ser) and threonine (Thr), and substituted analogs thereof;

X is a fluorine-free leaving group selected from the group consisting of phenoxy, substituted phenoxy and heterophenoxy;

E and G are one or more atoms more electronegative than carbon; and

D is hydrogen, methyl or a substituted methyl.

22 Claims, No Drawings

OTHER PUBLICATIONS van Noorden, Vogels and Smith, "Localization and Cytophotometric Analysis of Cathepsin B Activity in Unfixed and Undecalified Cryostat Sections of Whole Rat Knee Joints," 37 *J. Histochemistry and Cytochemistry* 617–624 (1989).

Delaissé, Eeckhout and Vaes, "In Vivo and In Vitro Evidence for the Involvement of Cysteine Proteinases in Bone Resorption," 125 *Biochemical and Biophysical Research Communications* 441–447 (1984).

Hayes, Stubberfield, McBride and Wilson, "Alterations in Cysteine Proteinase Content of Rat Lung Associated with Development of Pneumocystis Carinii Infection," 59 *Infection and Immunity* 3581–3588 (1991).

Cohen, Gregoret, Amiri, Aldape, Railey and McKerrow, "Arresting Tissue Invasion of a Parasite by Protease Inhibitors Chosen With The Aid of Computer Modeling," 30 *Biochemistry* 11221–11229 (1991).

Ashall, Harris, Roberts, Healy and Shaw, "Substrate Specificity and Inhibitor Sensitivity of a Trypanosomatid Alkaline Peptidase," 1035 *Biochimica et Biophysica Acta* 293–299 (1990).

Ashall, Angliker and Shaw, "Lysis of Trypanosomes by Peptidyl Fluoromethyl Ketones," 170 *Biochemical and Biophysical Research Communications* 923–929 (1990).

Rosenthal, Wollish, Palmer and Rasnick, "Antimalarial Effects of Peptide Inhibitors of a Plasmodium Falciparum Cysteine Proteinase," 88 *J. Clin Invest.* 1467–1472 (1991).

Smith, Rasnick, Burdick, Cho, Rose and Vahratian, "Visualization of Time–Dependent Inactivation of Human Tumor Cathepsin B Isozymes by a Peptidyl Fluoromethyl Ketone Using a Fluorescent Print Technique," 8 *Anti–cancer Research* 525–530 (1988).

Gordon and Mourad, "The Site of Activation of Factor X by Cancer Procoagulant," 2 *Blood Coagulation and Fibrinolysis* 735–739 (1991).

Cox, Cho, Eley and Smith, "A Simple, Combined Fluorogenic and Chromogenic Method for the Assay of Proteases in Gingival Crevicular Fluid," 25 *J. Periodont. Res.* 164–171 (1990).

Uitto, Larjava, Heino and Sorsa, "A Protease of Bacteroides Gingivalis Degrades Cell Surface and Matrix Glycoproteins of Cultured Gingival Fibroblasts and Induces Secretion of Collagenase and Plasminogen Activator," 57 *Infection and Immunity* 213–218 (1989).

Kunimatsu, Yamamoto, Ichimaru, Kato and Kato, "Cathepsins B, H and L Activities in Gingival Crevicular Fluid From Chronic Adult Periodontitis Patients and Experimental Gingivitis Subjects," 25 *J Periodont Res* 69–73 (1990).

Beighton, Radford and Naylor, "Protease Activity in Gingival Crevicular Fluid From Discrete Periodontal Sites in Humans With Periodontitis or Gingivitis"; 35 *Archs oral Biol.* 329–335 (1990).

Cox and Eley, "Preliminary Studies on Cysteine and Serine Proteinase Activities in Inflamed Human Gingiva Using Different 7–Amino–4–Trifluoromethyl Courmarin Substrates and Protease Inhibitors," 32 *Archs oral Biol.* 599–605 (1987).

(List continued on next page.)

OTHER PUBLICATIONS

Eisenhauer, Hutchinson, Javed and McDonald, "Identification of a Cathepsin B-Like Protease in the Crevicular Fluid of Gingivitis Patients," 62 *J Dent Res* 917 (1983).

von Figura, Steckel, Conary, Hasilik and Shaw, "Heterogeneity in Late-Onset Metachromatic Leukodystrophy. Effect of Inhibitors of Cysteine Proteinases," 39 *Am J Hum Genet.* 371-382 (1986).

Valentine, Winand, Pradhan, Moise, de Lahunta, Kornegay and Cooper, "Canine X-Linked Muscular Dystrophy as an Animal Model of Duchenne Muscular Dystrophy: A Review," 42 *Am J Hum Genet* 352-356 (1992).

Knott, Orr, Montgomery, Sullivan and Weston, "the Expression and Purification of Human Rhinovirus Protease 3C," 182 *Eur. J. Biochem.* 547-555 (1989).

Baricos, O'Connor, Cortez, Wu and Shah, "The Cysteine Proteinase Inhibitor, E-64, Reduces Proteinuria in an Experimental Model of Glomerulonephritis," 155 *Biochemical and Biophysical Research Communications* 1318-1323 (1988).

Dahlmann, Rutschmann, Kuehn and Reinauer, "Activation of the Multicatalytic Proteinase from Rat Skeletal Muscle by Fatty Acids or Sodium Dodecyl Sulphate," 228 *Biochem. J.* 171-177 (1985).

Kaltenbronn, "Renin Inhibitors Containing Isosteric Replacements of the Amide Bond Connecting the $P_3$ and $P_2$ Sites," 33, *J. Med. Chem.*, 838-841 (1990).

Krantz, et al. Copp, Coles, Smith and Heard, "Peptidyl (Acyloxy)methyl Ketones and the Quiescent Affinity Label Concept: The Departing Group as a Variable Structural Element in the Design of Inactivators of Cysteine Proteinases," 30 *Biochemistry* 4678-4687 (1991).

Smith, Copp, Coles, Pauls, Robinson, Spencer, Heard and Krantz, "New Inhibitors of Cysteine Proteinases. Peptidyl Acyloxymethyl Ketones and the Quiescent Nucleofuge Strategy," 110 *J. Am. Chem. Soc.* 4429-4431 (1988).

Shaw, Wikstrom and Ruscica, "An Exploration of the Primary Specificity Site of Cathepsin B," 222 *Archives of Biochemistry and Biophysics* 424-429 (1983).

Shaw, "Cysteinyl Proteinases and Their Selective Inactivation," 63 *Advances in Enzymology and Related Areas of Molecular Biology* 271-347 (1990).

CYSTEINE PROTEASE INHIBITORS EFFECTIVE FOR IN VIVO USE

BACKGROUND OF THE INVENTION

The present invention relates generally to peptidyl ketone inhibitors, and more particularly to peptidyl ketone inhibitors designed for the in vivo management of cysteine proteases, particularly cathepsin B and L, and their primitive enzymatic counterparts.

Cathepsins B and L are cysteinyl proteases involved in normal protein degradation. As such, they are generally located in the lysosomes of cells. When these enzymes are found extralysosomally they have been implicated by use of synthetic substrate technology and by natural endogenous inhibitors as playing a causative role in a number of disease states such as rheumatoid arthritis, osteo arthritis, pneumocystis carinii, schistosomiasis, trypanosoma cruzi, trypanosoma brucei bruci, Crithidia fusiculata, malaria, periodontal disease, tumor metastasis, metachromatic leukodystrophy, muscular dystrophy, etc. In particular, a connection between cathepsin B-type enzymes and rheumatoid arthritis has been suggested in van Noorden and Everts, "Selective Inhibition of Cysteine Proteinases by Z-Phe-Ala-CH$_2$F Suppresses Digestion of Collagen by Fibroblasts and Osteoclasts," 178 *Biochemical and Biophysical Research Communications* 178; Rifkin, Vernillo, Kleekner, Auszmann, Rosenberg and Zimmerman, "Cathepsin B and L Activities in Isolated Osteoclasts," 179 *Biochemical and Biophysical Research Communications* 63; Grinde, "The Thiol Proteinase Inhibitors, Z-Phe-Phe-CHN$_2$ and Z-Phe-Ala-CHN$_2$, Inhibit Lysosomal Protein Degradation in Isolated Rat Hepatocytes," 757 *Biochimica et Biophysica Acta* 15; Mason, Bartholomew and Hardwick, "The Use of Benzyloxycarbonyl[$^{125}$I]iodotyrosylalanyldiazomethane as a Probe for Active Cysteine Proteinases in Human Tissues," 263 *Biochem. J.* 945; van Noorden, Smith and Rasnick, "Cysteine Proteinase Activity in Arthritic Rat Knee Joints and the Effects of a Selective Systemic Inhibitor, Z-Phe-Ala-CH$_2$F," 15 *J. Rheumatol.* 1525; and van Noorden, Vogels and Smith, "Localization and Cytophotometric Analysis of Cathepsin B Activity in Unfixed and Undecalified Cryostat Sections of Whole Rat Knee Joints," 37 *J. Histochemistry and Cytochemistry* 617. A connection between cathepsin B and osteo arthritis has been suggested in Delaissé, Eeckhout and Vaes, "In Vivo and In Vitro Evidence for the Involvement of Cysteine Proteinases in Bone Resorption," 125 *Biochemical and Biophysical Research Communications* 441; a connection between cathepsin B and pneumocystis carinii has been suggested in Hayes, Stubberfield, McBride and Wilson, "Alterations in Cysteine Proteinase Content of Rat Lung Associated with Development of Pneumocystis Carinii Infection," 59 *Infection and Immunity* 3581; a connection between cysteine proteinases and schistosomiasis has ben suggested in Cohen, Gregoret, Amiri, Aldape, Railey and McKerrow, "Arresting Tissue Invasion of a Parasite by Protease Inhibitors Chosen With the Aid of Computer Modeling." 30 *Biochemistry* 11221. A connection between cysteine proteinases and trypanosoma cruzi, trypanosoma brucei brucei and crithidia fasciculata has been suggested in Ashall, Harris, Roberts, Healy and Shaw, "Substrate Specificity and Inhibitor Sensitivity of a Trypanosomatid Alkaline Peptidase," 1035 *Biochimica et Biophysica Acta* 293, and/or in Ashall, Angliker and Shaw, "Lysis of Trypanosomes by Peptidyl Fluoromethyl Ketones," 170 *Biochemical and Biophysical Research Communications* 923. A connection between cysteine proteinases and malaria has been suggested in Rosenthal, Wollish, Palmer and Rasnick, "Antimalarial Effects of Peptide Inhibitors of a Plasmodium Falciparum Cysteine Proteinase," 88 *J. Clin. Invest.* 1467, and in Rosenthal, Lee and Smith, "Inhibition of a Plasmodium Vinckei Cysteine Proteinase Cures Murine Malaria," (in press). A connection between cathepsin B and tumor metathesis has been suggested in Smith, Rasnick, Burdick, Cho, Rose and Vahratian, "Visualization of Time-Dependent Inactivation of Human Tumor Cathepsin B Isozymes by a Peptidyl Fluoromethyl Ketone Using a Fluorescent Print Technique," 8 *Anti-cancer Research* 525. A connection between cathepsin B and cancer has been suggested in Gordon and Mourad, 2 *Blood Coagulation and Fibrinolysis* 735. A connection between cathepsin B and periodontal disease has been suggested in Cox, Cho, Eley and Smith, "A Simple, Combined Fluorogenic and Chromogenic Method for the Assay of Proteases in Gingival Crevicular Fluid," 25 *J. Periodont. Res.* 164; Uitto, Larjava, Heino and Sorsa, "A Protease of Bacteriodes Gingivalis Degrades Cell Surface and Matrix Glycoproteins of Cultured Gingival Fibroblasts and Induces Secretion of Collagenase and Plasminogen Activator," 57 *Infection and Immunity* 213; Kunimatsu, Yamamoto, Ichimaru, Kato and Kato, "Cathepsins B, H and L Activities in Gingival Crevicular Fluid From Chronic Adult Periodontitis Patients and Experimental Gingivitis Subjects," 25 *J Periodont Res* 69; Beighton, Radford and Naylor, "Protease Activity in Gingival Crevicular Fluid From Discrete Periodontal Sites in Humans With Periodontitis or Gingivitis"; 35 *Archs oral Biol.* 329; Cox and Eley, "Preliminary Studies on Cysteine and Serine Proteinase Activities in Inflamed Human Gingiva Using Different 7-Amino-4-Trifluoromethyl Courmarin Substrates and Protease Inhibitors," 32 *Archs oral Biol.* 599; and Eisenhauer, Hutchinson, Javed and McDonald, "Identification of a Cathepsin B-Like Protease in the Crevicular Fluid of Gingivitis Patients," 62 *J Dent Res* 917. A connection between cathepsin B and metachromatic leukodystrophy has been suggested in von Figura, Steckel, Conary Hasilik and Shaw, "Heterogeneity in Late-Onset Metachromatic Leukodystrophy. Effect of Inhibitors of Cysteine Proteinases," 39 *Am J Hum Genet.* 371; a connection between cathepsin B and muscular leukodystrophy has been suggested in Valentine, Winand, Pradhan, Moise, de Lahunta, Kornegay and Cooper, "Canine X-Linked Muscular Dystrophy as an Animal Model of Duchenne Muscular Dystrophy: A Review," 42 *Am J Hum Genet* 352; a connection between cathepsin B and rhinovirus has been suggested in Knott, Orr, Montgomery, Sullivan and Weston, "The Expression and Purification of Human Rhinovirus Protease 3C," 182 *Eur. J. Biochem.* 547; a connection between cathepsin B and kidney disease has been suggested in Baricos, O'Connor, Cortez, Wu and Shah, "The Cysteine Proteinase Inhibitor, E-64, Reduces Proteinuria in an Experimental Model of Glomerulonephritis," 155 *Biochemical and Biophysical Research Communications* 1318; and a connection between cathepsin B and multiple sclerosis has been suggested in Dahlman, Rutschmann, Kuehn and Reinauer, "Activation of the Multicatalytic Proteinase from Rat Skeletal Muscle by Fatty Acids or Sodium Dodecyl Sulphate," 228 *Biochem. J.* 171.

Although a number of cysteine proteinase inhibitors have been identified, most of these have drawbacks for in vivo use. In particular, drawbacks such as reversibility of inhibition, lack of specificity, and rapid clearance from the body have been associated with prior art inhibitors. The microbial products antipain and leupeptin, for example, are effective but reversible inhibitors of cysteine proteinase (McConnell et al., 33 *J. Med. Chem.* 86–93; Sutherland et al. 110 *Biochem. Biophys. Res. Commun.* 332–38), and also inhibit certain serine proteinases (Umezawa, 45 *Meth. Enzymol.* 678–95). The compound E64 and its synthetic analogues are more selective inhibitors (see, e.g., Barret et al., 201 *Biochem. J.* 189–98, and Grinde, 701 *Biochem. Biophys. Acta.* 328–33), but disappear too quickly from the circulation for in vivo use (Hashida et al. 91 *J. Biochem.* 1373–80).

The most promising type of cysteine proteinase inhibitors have an activated carbonyl with a suitable α-leaving group fused to a programmed peptide sequence that specifically directs the inhibitor to the active site of the targeted enzyme. Once inside the active site, the inhibitor carbonyl is attached by a cysteine thiolate anion to give the resulting hemiacetal. If the α-leaving group then breaks off, the bond between enzyme and inhibitor becomes permanent and the enzyme is irreversibly inactivated.

The usefulness of an inhibitor in inactivating a particular enzyme therefore depends not only on the "lock and key" fit of the peptide portion, but also on the reactivity of the bond holding the α-leaving group to the rest of the inhibitor. It is important that the leaving group be reactive only to the intramolecular displacement via a 1,2-migration of sulfur in the breakdown of the hemithioacetal intermediate.

Groundbreaking work regarding cysteine proteinase inhibitors having an activated carbonyl, a suitable α-leaving group and a peptide sequence effective to specifically direct the inhibitor to the active site of the targeted enzyme was disclosed in U.S. Pat. No. 4,518,528 to Rasnick, incorporated herein by reference. That patent established peptidyl fluoromethyl ketones to be unprecedented inhibitors of cysteine proteinase in selectivity and effectiveness. The fluoromethyl ketones described and synthesized by Rasnick included those of the formula:

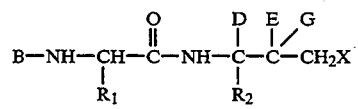

wherein $R_1$ and $R_2$ are independently selected from the group hydrogen, alkyl of 1–6 carbons, substituted alkyl of 1–6 carbons, aryl, and alkylaryl where the alkyl group is of 1–4 carbons; n is an integer from 1–4 inclusive; X is a peptide end-blocking group; and Y is an amino acid or peptide chain of from 1–6 amino acids.

Peptidylketone inhibitors using a phenol leaving group are similar to the peptidyl fluoroketones. As is known in the art, oxygen most closely approaches fluorine in size and electronegativity. Further, when oxygen is bonded to an aromatic ring these values of electronegativity become even closer due to the electron withdrawing effect of the sp2 carbons. The inductive effect of an α-ketophenol versus an α-ketofluoride when measured by the pKa of the α-hydrogen, appears comparable within experimental error.

Although the general association between various disease states and cysteine proteinase inhibitors is known, the prior art has not identified specific methods of treatment using specific inhibitors of the type first described by Rasnick. A need therefore exists for methods of treating various disease states characterized by extralysosomal cathepsin B and/or cathepsin L activity. The present invention addresses that need.

SUMMARY OF THE INVENTION

Briefly describing the present invention, there is provided a method of treating medical conditions which are characterized by extralysosomal cathepsin B and/or cathepsin L activity. In particular, a group of cathepsin B and/or cathepsin L inhibitors which have been shown to be particularly effective in in vivo applications is disclosed.

Concerning the specific compound employed in the present invention, preferred compounds have the formula:

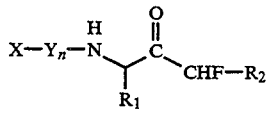

wherein

B is H or an amino acid blocking group for the N-terminal amino acid nitrogen;

$R_1$ is an optionally protected α-amino acid side chain on the $P_2$ amino acid residue, and is selected such that the $P_2$ amino acid residue is the residue of an α-amino acid selected from the group consisting of phenylalanine (Phe), leucine (Leu), tyrosine (Tyr) and valine (Val), and substituted analogues thereof, particularly including Tyr(OMe);

$R_2$ is an optionally protected α-amino acid side chain on the $P_1$ amino acid residue, and is selected such that the $P_1$ amino acid residue is the residue of an α-amino acid selected from the group consisting of alanine (Ala), arginine (Arg), aspartic acid (Asp), glutamic acid (Glu), histidine (His), homophenylalanine (HPhe), phenylalanine (Phe), ornithine (Orn), serine (Ser) and threonine (Thr), and substituted analogues thereof;

X is a fluorine-free leaving group selected from the group consisting of phenoxy, substituted phenoxy and heterophenoxy;

E and G are atoms more electronegative than carbon, wherein E and G may be the same atom, as in a carbonyl or hydrazone, bonded to the peptide chain by a double bond, or two separate atoms each bonded to the peptide chain by a single bond; and D is hydrogen, methyl or a substituted methyl.

One object of the present invention is to provide a method of treating medical conditions which are characterized by extralysosomal cathepsin B and/or cathepsin L.

A further object of the present invention is to provide a group of cathepsin B and/or cathepsin L inhibitors which are particularly effective for in vivo applications.

Further objects and advantages of the present invention will be apparent from the following description.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to method of treating medical conditions which are characterized by extralysosomal cathepsin B and/or cathepsin L. In one aspect of the invention, a group of cathepsin B and/or cathepsin L inhibitors which have been shown to be particularly effective in in vivo applications is disclosed.

The inhibitors of the present invention can be described generally by the formula:

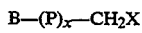

wherein
- B is an amino acid blocking group for the N-terminal amino acid,
- each $(P)_x$ is an optionally protected $\alpha$-amino acid residue, and
- X is a leaving group.

As is conventional in the art, and as used herein, amino acid residues may be designated as $P_1$, $P_2$, etc., wherein $P_1$ refers to the amino acid residue nearest the leaving group, $P_2$ refers to the amino acid residue next to $P_1$ and nearer the blocking group, etc. In dipeptide inhibitors therefore, $P_2$ is the amino acid residue nearest the blocking group.

More specifically, the compounds employed in the present invention are of the formula:

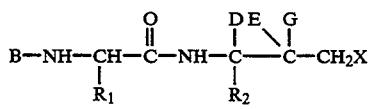

wherein
- B is H or an amino acid blocking group for the N-terminal amino acid nitrogen;
- $R_1$ is an optionally protected $\alpha$-amino acid side chain on the $P_2$ amino acid residue, and is selected such that the $P_2$ amino acid residue is the residue of an $\alpha$-amino acid selected from the group consisting of phenylalanine (Phe), Leucine (Leu), tyrosine (Tyr) and valine (Val), and substituted analogues thereof, particularly including Tyr(OMe);
- $R_2$ is an optionally protected $\alpha$-amino acid side chain on the $P_1$ amino acid residue, and is selected such that the $P_1$ amino acid residue is the residue of an $\alpha$-amino acid selected from the group consisting of alanine (Ala), arginine (Arg), aspartic acid (Asp), glutamic acid (Glu), histidine (His), homophenylalanine (HPhe), phenylalanine (Phe), ornithine (Orn), serine (Ser) and threonine (Thr), and substituted analogues thereof;
- X is a fluorine-free leaving group selected from the group consisting of phenoxy, substituted phenoxy and heterophenoxy;
- E and G are atoms more electronegative than carbon, wherein E and G may be the same atom, as in a carbonyl or hydrazone, bonded to the peptide chain by a double bond, or two separate atoms each bonded to the peptide chain by a single bond; and
- D is hydrogen, methyl or a substituted methyl.

Concerning the amino acid blocking group B for the N-terminal amino acid nitrogen, many suitable peptide end-blocking groups are known in the art. For example the end-blocking groups identified in E. Gross and J. Meienhofer (eds.), *The Peptides*, Vol. 3 are generally suitable for use in the present invention. Preferred blocking groups include N-morpholine carbonyl and derivatives of propionic acid derivatives that have intrinsic analgesic or anti-inflammatory action. Examples of blocking groups having intrinsic analgesic or anti-inflammatory action may be found in Gilman, Goodman, Gilman, *The Pharmacological Basis of Therapeutics*, Sixth Ed. MacMillan, Chapter 29. As defined herein, the peptide end-blocking group is attached to either an amino acid or a peptide chain.

One particularly effective blocking group is the 4-morpholinylcarbonyl blocking group shown below:

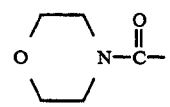

4-morpholinylcarbonyl

Concerning the side chain on the $P_2$ amino acid, such side chains are selected so that the linked $P_2$ amino acid is a member of the group consisting of phenylalanyl (Phe), leucyl (Leu), tyrosyl (Tyr) and valyl (Val) amino acid residues and substituted analogues thereof, particularly including Tyr(OMe). Extensive testing of various side chains on the $P_2$ amino acid has identified this group of side chains as providing superior safety and efficacy for in vivo applications such as are described herein. This superior safety and efficacy could not have been predicted from the prior art, and was established only after extensive experimentation.

Side chains appropriate for forming such amino acid residues include:

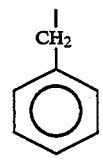

phenylalanyl

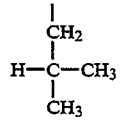

leucyl

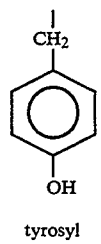

tyrosyl

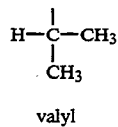

valyl

Concerning the side chain on the $P_1$ amino acid, such side chains are selected so that the linked $P_1$ amino acid is a member of the group consisting of alanyl (Ala), arginyl (Arg), aspartic acid (Asp), glutamic acid (Glu), histidyl (His), homophenylalanyl (HPhe), phenylalanyl (Phe), ornithyl (Orn), seryl (Ser) and threonyl (Thr), and optionally substituted analogues thereof such as thiazoles and amino thiazoles.

It is to be appreciated from the prior art that other heterocycles can replace the histidyl imidazole without a loss of potency. Further, a number of modifications to the amidine base of arginine are commonly known. Accordingly, all five-and six-membered ring heterocycles with chain lengths of two to five carbon atoms and containing nitrogen, oxygen or sulfur are considered to be substituted analogues of $P_1$ amino acid residues for the purposes of the present invention.

In addition, it is known that ester and amide derivatives of the amino acid residues may be used without adversely affecting the suitability of the inhibitors for in vivo applications. Accordingly, such ester and amide derivatives of the above-named amino acid residues, particularly aspartic and glutamic acid residues, are intended to be included as substituted analogues within the scope of the present invention.

Again, extensive testing of various side chains on the $P_1$ amino acid has identified this group of side chains as providing superior safety and efficacy for in vivo applications such as are described herein. This superior safety and efficacy could not have been predicted from the prior art, and was established only after extensive experimentation.

Side chains appropriate for the $P_1$ amino acid include:

alanyl

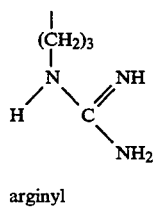

arginyl

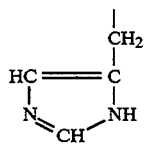

histidyl

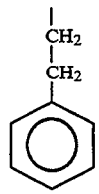

homophenylalanyl

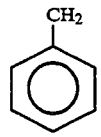

phenylalanyl

ornithyl

seryl

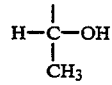

threonyl

Concerning the leaving groups of the present invention, such leaving groups are selected from the group consisting of phenoxy, substituted phenoxy and heterophenoxy. In particular, fluorine-free leaving groups are preferred. It is to be appreciated that when using phenol as the leaving group, the pool of available phenols includes anti-inflammatories such as aspirin and aspirin-like drugs, methyl salicylate, acetaminophen and other derivatives. Clearly, releasing such an anti-inflammatory to reduce prostoglandin production and/or pain is beneficial in certain circumstances. Suitable phenoxy, substituted phenoxy and heterophenoxy leaving groups for a specific application may be selected by those skilled in the art without undue experimentation.

It is also to be appreciated that during the course of the reaction of enzyme with inhibitor, the carbonyl of the inhibitor rehybridizes to sp3 and forms a ketal intermediate with the thiol function of the enzyme. Under the acid conditions of this reaction, other ketals can exchange with this intermediate either by going through the ketone or by ketal-ketal exchange. Accordingly, ketals can be substituted for carbonyls in the peptidyl inhibitors of the present invention. Similarly, other compounds such as hydrazones, hemiketals, oximes, imines, cyanohydrins, enolethers, enamines, hemithioketals, and the like are to be considered carbonyl equivalents and may be substituted for a carbonyl or to give a carbonyl under the acidic conditions of these inhibition reactions. Utilization of such derivatives can also be vehicles to either improve the bioavailability of the inhibitor drug or keep it from crossing a cellular membrane depending upon the hydrophobic nature of the masking function.

It is also to be appreciated that the development and synthesis of compounds having isosteric replacements of amide bonds is now a standard practice in the development of biologically active peptides once the optimum peptide sequence has been identified. Accordingly, the present invention includes compounds having one or more modified amide bonds in the peptide sequence so long as conformation and binding are maintained while secondary enzymatic hydrolysis is prevented. For a list of such modifications see Kaltenbronn, 33, *J. Med. Chem.*, 838. In addition, inhibitors having a hydrazine replacement for the $P_1$ nitrogen as reported by Giordano for other halogen methyl ketones are also intended to be claimed.

EXAMPLE 1

General procedure for the preparation of 4-Morpholine carbonyl-amino acid esters. To the pTSA salt of the amino acid benzyl ester (24.12 mmol) in THF (100 ml) is added 4-morpholine carbonyl chloride (Aldrich) 24.12 mmol, followed by N-methylmorpholine (48.24 mmol). The mixture is stirred at room temperature overnight, then is poured into 100 ml 1 N hydrochloric acid, extracted with ethyl acetate (200 ml), washed with saturated sodium bicarbonate solution (100 ml) and brine (40 ml), dried over magnesium sulfate, filtered, and finally evaporated to give the morpholine carbonyl benzyl ester. The free acid is obtained by reduction with hydrogen (30 psi), 10% palladium on carbon with ethyl acetate as the solvent.

EXAMPLE 2

(4-morpholinylcarbonyl)-L-phenylalanyl-L-homophenylalanyl-(2-carboxymethyl) phenoxymethyl ketone (MU-Phe-HPhe-O-Ph). To a solution of 4-morpholinecarbonyl-L-phenylalanine (8.3 mmol) in 100 ml THF at ($-15°$ C.) is added 1 equivalent (0.913 ml) N-methylmorpholine followed by isobutylchloroformate (8.3 mmol, 1.08 ml). Homophenylalanine methyl ester hydrochloride salt (8.4 mol, 1.94 g) is added after 10 min of reaction followed by another equivalent (0.913 ml) of N-methylmorphline. The reaction is allowed to come slowly to room temperature and is then stirred overnight. The reaction is poured into 100 ml HCl (1 N), extracted with ethyl acetate (200 ml), washed with 50 ml HCl (1 N) saturated sodium bicarbonate ($2\times100$ ml) and brine (100 ml), dried over MgSO$_4$, filtered and evaporated to give 3.50 g (93%) of a white foam.

The foam material is dissolve din 50 ml of methanol and 7.8 ml of 1 N sodium hydroxide. After 5 hr the solution is concentrated to a gum, diluted with water and extracted with ethyl acetate. The water fraction is then neutralized with 1 N HCl and extracted with ethyl acetate. The organic layer is dried (MgSO$_4$), filtered, and concentrated to dryness to give a white solid (2.65 g, 78%, m.p. 88°–96° C.).

General procedure for the conversion of N-blocked peptidyl free acids to N-blocked peptidyl bromomethyl ketones. One equivalent (0.495 ml, 4.5 mmol) of N-methylmorpholine is added to a solution of 4-morpholine carbonyl-phenylalanyl-homophenyl alanine (2.00 g, 4.5 mmol at $-15°$ C.). One equivalent (0.583 ml) of isobutyl chloroformate is thereafter added to the mix. The mixture is stirred at this temperature for 10 min and then added through filter paper to an etheral solution of diazomethane prepared from 4.3 g of Diazald according to the supplier's directions (Aldrich). After stirring overnight the reaction is washed with water ($2\times50$ ml), saturated sodium bicarbonate (50 ml) and brine (50 ml), dried over MgSO$_4$, filtered and evaporated to dryness. Purification by column chromatography (150 g, CHCl$_3$:isopropanol, 9:1) gives pure diazomethyl ketone characterized by the diazomethyl hydrogen absorption at 5.25 ppm.

Conversion to the bromomethyl ketone. One ml of a 30% solution of hydrogen bromide in acetic acid is diluted with 1 ml of methylene chloride and then added dropwise to a solution of 4-morpholine carbonylphenylalanyl-homophenyl alanyl diazo methyl ketone in 25 ml of methylene chloride at $-15°$ C. After 10 min, TLC monitoring shows a loss of starting material (Rf 0.35; silica gel, CHCl$_3$:isopropanol, 9:1). The reaction is poured into 150 ml of water and extracted with ethyl acetate ($2\times100$ ml). The combined organic fractions are washed with brine ($2\times50$ ml), sodium bicarbonate ($2\times50$ ml) and brine again ($2\times50$ ml), dried over Na$_2$SO$_4$ and concentrated to give 660 mg bromomethyl ketone (86% of a solid foam characterized by its NMR proton absorption at 3.82 ppm).

Preparation of phenoxymethyl ketones. Potassium fluoride (230 mg) is added to a flask containing 1 ml of DMF, 0.5 ml of methyl salicylate, and 1 g (2.2 mmol) of (4-morpholine carbonyl)-L-phenylalanyl-homophenylalanyl bromomethyl ketone. The reaction is then cooled, diluted with a solution of chloroform and isopropanol ((9:1), and passed through silica gel to remove the potassium fluoride. The filtrate is evaporated to dryness and chromatographed (75 g silica gel, CH$_2$Cl$_2$:methanol, 9:1) to give 0.9 g (79%) of solid phenoxymethyl ketone, m.p. 115°–121° C.

EXAMPLE 3 t-Butyl carbamyl-L-arginyl-(2-Carboxymethyl) phenoxymethyl ketone. In a method according to Example 2, potassium fluoride (40 mg) is added to 42 mg of BOC-Arg-CH$_2$Br and methyl salicylate (800 mg). The reaction is heated to 62° under argon for 11 min, cooled, diluted with ethyl acetate, washed with water, dried over Na$_2$SO$_4$, concentrated and precipitated from ether. The product has an Rf value of 0.5 (silica gel, CHCl$_3$:isopropanol, 8:2) and is five times as effective as Z-Phe-Ala-FK in inhibiting cathepsin B.

EXAMPLE 4 t-Butyloxycarbonyl-L-phenylalanyl-alanyl-bromomethyl ketone (BOC-Phe-Ala-bromomethyl ketone). To t-butyloxycarbonyl-L-phenylalanyl-2-carbamoyl-diazoketone (1.8 g, 5 mm) in 9 m methylene chloride at 0° C. is added in a dropwise manner 2.5 ml of 30% hydrogen bromide-acetic acid (Aldrich) which has been diluted to 5.5 ml with methylene chloride. This addition takes 2 hr at which time TLC shows the starting material to be lost (Rf 0.39). The reaction is quenched at 0° C. by adding 300 mg solid sodium bicarbonate. Water (5 ml) is added and the mixture is extracted with 30 ml methylene chloride. The organic fraction is washed with 15 ml water, dried over MgSO$_4$ and concentrated under vacuum to give 1.5 g (75%) of crude bromide product. Column chromatography (silica gel, hexane:ethyl acetate, 1:1) gives 1 g pure bromoketone, (mp 129°14 130° C., Rf 0.47), NMR (CHCl$_3$) δ 1.33 (d, 3 H, J=7 Hz), 1.40 (s, 9 H), 3.10 (d, J=14 Hz), 4.00 (s, 2 H), 4.40 (m, 1 H), 4.81 (m, 1 H), 5.15 (m, 1 H), 6.70 (m, 1 H), 7.45 (m, 5 H).

EXAMPLE 5

N-Benzyloxycarbonyl-L-alanyl bromomethylketone (Z-Ala-bromomethyl ketone). This bromoketone is made in the manner of the bromoketone of Example 4 except that N-benzyloxycarbonyl-2-carbamoyl-diazoketone is used as a starting material. The following results obtain: 40% yield, Rf 0.48, mp 72°–75° C., NMR (CHCl$_3$) δ 1.43 (d, 3 H, J=7 Hz), 4.06 (s, 2 H), 4.66 (m, 1 H), 5.12 (s, 2 H), 7.26–7.35 (m, 5 H).

EXAMPLE 6

N-t-Butyloxycarbonyl L-phenylalanyl-alanine-2-methoxycarbonyl phenoxymethyl ketone. The bromoketone of Example 4 (500 mg, 1.2 mm) is mixed with potassium fluoride (137 mg, 2.4 mm), methyl salicylate 357 mg, 2.3 mm) and 2.8 ml DMF under argon at 35° C. for 1 hr. The reaction mixture is diluted in 50 ml ethyl acetate and the organic portion is washed with water (3×25 ml), dried over MgSO$_4$ and concentrated to 1 g. Purification by column chromatography (silica gel, hexane:ethyl 1:1, Rf 0.465) yields 306 mg N-t-butyloxycarbonyl L-phenylalanyl-alanine-2-methoxycarbonyl phenoxymethyl ketone (56%), mp 102.9°–106.6° C. NMR (CDCl$_3$) δ 1.40 (s, 9 H), 1.45 (d, 3 H), 3.09 (m, 1 H), 3.95 (s, 3 H), 4.55 (d, 2 H), 5.10 (m, 1 H); MS, m/e (485, MH+).

EXAMPLE 7

N-BOC-Phe-Ala-phenoxymethyl ketone. This compound is made in the same manner as the compound of Example 6 except that the reagent concentrations are: BOC-Phe-Ala-bromoketone (120 mg, 0.29 mm), potassium fluoride (150 mg, 2.5 m), phenol (180 mg, 1.9 mm) and DMF (0.5 ml). Reaction yield is 85%; mp 117.5° C.; MS m/e (427.30, MH+); NMR (CDCl$_3$) δ 1.40–1.50 (d, J=8 Hz), 1.42 (s, 9), 3.10 (d, 2 H), 4.40 (m, 1 H), 4.75 (s, 2 H), 4.50–5.50 (m, 4 H), 6.50–7.50 (m, 10 H).

EXAMPLE 8

Z-Ala-phenoxymethyl ketone. This compound is made in the same manner as the compound of Example 6 except that the reagent concentrations are: bromoketone (300 mg), 0.88 mm), potassium fluoride (100 mg, 0.17 mmol), 0.3 ml dry DMF and methyl salicylate (260 mg, 1 mmol). The mixture is then heated under argon for 10 min at 98° C., cooled to 0° C., diluted with 10 ml water and extracted with 5 ml ethyl acetate. The organic layer is washed with 10 ml water, dried over MgSO$_4$, concentrated and purified by TLC (hexane:ethyl acetate, 1:1), silica gel with the product collected at Rf 0.42. Yield after column chromatography is 150 mg (46%). NMR (CDCl$_3$) δ 1.57 (d, 3 H, J=7 Hz), 4.05 (s, 3 H), 4.66 (s, 2 H), 4.92 (m, 1 H), 5.21 (s, 2 H), 6.05 (m, 1 H), 6.60–8.10 (m, 8 H). MS m/e (371, MH+). Anal. C (63.72), H (5.65), N (4.33); calc. C (64.68), H (5.69), N (3.77).

EXAMPLE 9

Synthesis of Morpholine carbonyl phenylalanyl 2-aminoisobutyric methyl phenoxy ketone Synthesis of 2-aminoisobutyric methylester HCl salt. To 2-aminoisobutyric acid in 125 ml of methanol is added 125 ml of methanol saturated with HCl. The initial mixture becomes a solution and the reaction is sealed and allowed to stir at room temperature overnight. The next day the reaction is evaporated, first neat and then from toluene to give a solid.

Synthesis of morpholine carbonyl 2-aminoisobutyric acid. Morpholine carbonyl phenylalanine (3.6 g, 0.013 mmol) in 200 ml of THF is cooled to −20° C. under argon. One equivalent of N-methylmorpholine followed by one equivalent of isobutyl chloroformate is added and the reaction is stirred under argon for 10 min. The hydrochloride salt of methylalanine methyl ester is added to the mix, followed by 1.2 equivalents of N-methylmorpholine. The reaction is allowed to come slowly to room temperature and is stirred overnight. The reaction is poured into an equal volume of 1 N hydrochloric acid and extracted with ethyl acetate (2×100 ml). The combined extracts are washed with aqueous sodium bicarbonate (2×50 ml) and dried over sodium sulfate. The solvent is evaporated to the methyl ester as a white solid, m.p. 174°–188° C.

Conversion to the acid. Morpholine carbonyl-2-aminoisobutyric methyl ester (5.65 mmol) is dissolved in 60 ml of methanol containing 6 ml (1 N) sodium hydroxide and is stirred under argon overnight. The reaction is then concentrated, diluted with ethyl acetate and extracted with water (50 ml) containing 7 ml 1 N sodium hydroxide. The water is neutralized and extracted with ethyl acetate, and is then dried (Na$_2$SO$_4$) and concentrated to give a white solid, m.p. 162°–166° C.

The acid is then converted to the 2-carbomethoxy phenoxymethylketone as previously described in Example 2. The relative inhibition of cathepsin B for this inhibitor is 0.2 times that of Z-Phe-Ala-CH$_2$F.

EXAMPLE 10

Synthesis of peptidyl methylfluoroketone ketals: synthesis of the ketal of Mu-Phe-HPhe fluoromethyl ketone. Ethylene gycol (25 ml) is dehydrated by heating at 140° C. for one hour under a stream of nitrogen. The temperature is then reduced to 70° C. and 1.8 g of pTSA as added followed by 310 mg (0.69 mmol) of Mu-Phe-HPhe methylfluoroketone. After 1 hr TLC (CHCl$_3$:MeOH, 9:1) on silica gel showed a product of Rf 0.433 above the starting material Rf 0.396. The reaction is poured into twice its volume of sodium bicarbonate and ice. The resulting mixture is extracted twice with 50 ml ethyl acetate. The combined organic layers are washed with brine, dried over MgSO$_4$ and concentrated to give a solid foam. The product may be chromatographed (200 g silica gel, CHCl$_3$:isopropanol, 9:1) to give a high yield of ketal which was shown to be free from the ketone by a single triplet (−221.35 ppm) in the fluorine NMR. (Ketone triplet 220.55 ppm).

EXAMPLE 11

Preparation of modified arginine derivative at P$_1$: synthesis of Mu-Phe-δ-(4,6-dimethyl-2-pyrimidyl) ornithine methyl ester. In a 250 ml round bottom flask was placed 1.08 mmol of Mu-Phe-OH in 100 ml THF. The solution was cooled under argon to −20° and one equivalent of N-methylmorpholine and one equivalent of isobutyl chloroformate were added. After 10 min δ-(4,6-dimethyl-2-pyrimidyl) ornithine methyl ester hydrochloride salt (prepared in the manner of Gilbert and Leary, Biochemistry. vol. 14, pp. 5194–99), was added followed by one more equivalent of N-methylmorpholine. The next day the reaction is poured into water and extracted with ethyl acetate. The organic layer was dried ($Na_2SO_4$) and concentrated to give 130 mg of a while solid. $R_f$(CHCl$_3$:isopropanol, 8:2)=0.43. This material was saponified with one equivalent of 1 N sodium hydroxide in the usual way and taken to the phenoxy ketone as in Example 2.

EXAMPLE 12

Determination of Surprisingly Effective Proteinase Inhibitors. Cathepsin B. purified from human liver, was obtained from Enzyme Systems Products (Dublin, Calif.). The activity of the enzyme used in this Example was 50 mU per ml at 30° C. in 50 mm sodium phosphate buffer, pH 6.2, 5 mm DTT, 2 mm EDTA, with Z-Leu-Arg-Arg-7-amino-4-trifluoromethyl courmarin (Z-Leu-Arg-Arg-AFC) as substrate.

Cathepsin B assays were done under the following conditions: Five μl of enzyme stock solution was preincubated with 435 μl of phosphate buffer for 30 minutes to activate the enzyme. Nine μl of 20 mm stock substrate solution (in dimethylformamide) were added and mixed with the activated enzyme. Activity was followed by the release of free AFC as monitored by a Perkin-Elmer LS-5B spectrofluorometer (excitation=400 nm, emission=505 nm).

The inhibitors described herein were prepared in 20 mm stock solutions in DMF. Five μl aliquots of each inhibitor were added to the enzyme 2 min before the substrate was added to the mix. Potency was determined relative to the activity of a standard cathepsin B inhibitor, Z-Phe-Ala-CH$_2$F (relative potency of 1.0).

It was determined that inhibitors having a side chain on the P$_2$ amino acid selected from the group consisting of phenylalanyl (Phe), leucyl (Leu), tyrosyl (Tyr), valyl (Val) and substituted analogues thereof, including Tyr-(OMe), were particularly effective against cathepsin B. Further, inhibitors with a side chain on the P$_1$ amino acid selected from the group consisting of alanyl (Ala), arginyl (Arg), histidyl (His), homophenylalanyl (HPhe), phenylalanyl (Phe), ornithyl (Orn), seryl (Ser), threonyl (Thr), thiazoles and amino thiazoles and modifications thereof including 4,6-dimethyl or 4,6-dihydroxy pyrimidyl, and substituted analogues thereof, were also particularly effective. The relative potencies of such tested compounds were typically between 2.0 and 10.0, with relative potencies in excess of 25.0 being observed for some compounds. The potencies of members of this relatively small class of inhibitors, those having P$_1$ and P$_2$ amino acid side chains selected from the above-described groups, were surprisingly high relative to the potencies of inhibitors with alternative side chains.

EXAMPLE 13

Treatment of Rheumatoid Arthritis with Mu-Phe-HPhe-O-Ph.

DBA/Lac mice were injected with 200 μg of type II chick collagen emulsified in Freund's complete adjuvant on day 0 and on day 21. Mu-Phe-HPhe-O-Ph was suspended in an ethanol solution which was then diluted to 10% (aq) and administered by gavage at a dose of 10 mg/kg/day from day 21 until sacrifice at day 49. The severity of joint inflammation was evaluated grossly at seven day intervals beginning on day 21.

The effect of oral administration of Mu-Phe-HPhe-O-Ph on the severity of bone lesions in adjuvant-induced arthritis wa determined by evaluating osseous mineralization, periostat proliferation, bone erosion, joint space narrowing and osseous fragmentation. All lesions were scored on a scale of 0 (normal architecture) to 3 (severe or marked changes). Values calculated were means values ±1 std. error of the mean. The "bone lesion severity" values of Mu-Phe-HPhe-O-Ph treated animals were significantly (p<0.05) lower than the values of control animals for each parameter tested.

The effect of oral administration of Mu-Phe-HPhe-O-Ph on the histological aspects of adjuvant-induced arthritis was determined by evaluating inflammation, focul ulcers, tibiotarsal joint cartilage destruction, bone destruction and periosteal proliferation. Inflammation was scored on a scale of 0 (no inflammation) to 3 (severe) based on the extent of edema and cell infiltration. Focul ulcer cartilage destruction was measured as the percent of articular cartilage surfaces with focal destruction which exposed underlying subchondral bone. Tibiotarsal joint cartilage destruction was measured as the percent of articulating surfaces with destruction of the subchondral bone. Values calculated were mean values ±1 std. error of the mean. The "histological aspects" values of Mu-Phe-HPhe-O-Ph treated animals were significantly (p<0.05) lower than the values of control animals for each parameter tested.

EXAMPLE 14

Treatment of Rheumatoid Arthritis with Mu-Phe-HPhe-O-Ph.

DBA/Lac mice were injected with 200 μg of type II chick collagen emulsified in Complete Freund's Adjuvant on day 0 and on day 21. Mu-Phe-HPhe-O-Ph was suspended in phosphate buffered saline and administered by gavage from day 21 until sacrifice at day 35. Doses of between 3 mg/kg/day and 25 mg/kg/day were used, with the daily dosage being held constant over time for each test. The severity of joint inflammation was evaluated grossly at seven day intervals beginning on day 21.

The effect of oral administration of Mu-Phe-HPhe-O-Ph on the severity of bone lesions in adjuvant-induced arthritis was determined by evaluating osseous mineralization, periostat proliferation, bone erosion, joint space narrowing and osseous fragmentation. All lesions were scored on a scale of 0 (normal architecture) to 3 (severe or marked changes). Values calculated were mean values ±1 std. error of the mean. The "bone lesion severity" values of Mu-Phe-HPhe-O-Ph treated animals were significantly (p<0.05) lower than the values of control animals for each parameter tested.

EXAMPLE 15

Treatment of Rheumatoid Arthritis with Mu-Tyr-(OMe)-HPhe-O-Ph. Rats were injected with adjuvant on day 0 and were treated with Mu-Tyr(OMe)-HPhe-O-Ph in ground diet from the time of adjuvant injection until sacrifice at day 32. Over the course of the disease, animals were evaluated in terms of a mean clinical score, a derived series of clinically observed parameters normalized to facilitate graphical presentation. Mean paw volumes were also measured using normalized units throughout the course of the disease. At the end of the study, the animal groups were sacrificed and evaluated by X-ray analysis.

The mean clinical scores of Mu-Tyr(OMe)-HPhe-O-Ph treated rats were significantly lower than the scores for untreated animals. Similarly, mean paw volumes were also significantly reduced. This Example demonstrates the beneficial effect of Mu-Tyr(OMe)-HPhe-O-Ph on adjuvant-induced arthritis.

EXAMPLE 16

Treatment of Osteo Arthritis with Mu-Phe-HPhe-O-Ph. The skeletons of young growing rats were radioactively labelled by injections with $^{14}$C-tetracycline over a 10 day period. The amount of bone resorption was then determined each day as the amount of radioactivity excreted in the urine. After 10 days of control excretion, test compounds were administered for three days subcutaneously and their effects on the daily excretion of tetracycline were determined. Tested compounds were dissolved in DMSO/PEG at a concentration of 25 mg/ml and were injected once per day subcutaneously in a volume of 2 ml/kg.

Mu-Phe-HPhe-O-Ph inhibited bone resorption in vivo as measured by tetracycline excretion. The effect was as great as that of a maximal dose of calcitonin. The onset of inhibition was rapid, with the maximum effect occurring only 24 hours after dosing commenced.

At the end of the experiment, lesions were visible at the sits of injection. Histological evaluation revealed extensive inflammation of the subcutaneous fat layer extending into the overlying dermis and underlying muscle layers. Tissue necrosis was also observed.

EXAMPLE 17

Treatment of Osteo Arthritis with Mu-Leu-HPhe-O-Ph. The skeletons of young growing rats were radioactively labelled by injections with $^{14}$C-tetracycline over a 10 day period. The amount of bone resorption was then determined each day as the amount of radioactivity excreted in the urine. After 10 days of control excretion, test compounds were administered for three days subcutaneously and their effects on the daily excretion of tetracycline were determined. Tested compounds were dissolved in DMSO/PEG at a concentration of 25 mg/ml and were injected once per day subcutaneously in a volume of 2 ml/kg.

Mu-Leu-HPhe-O-Phe inhibited bone resorption in vivo as measured by tetracycline excretion. The effect was nearly as great as that of a maximal dose of calcitonin, but was not quite as great as that of Mu-Phe-HPhe-O-Ph. Again, the onset of inhibition was rapid, with the maximum effect occurring only 24 hours after dosing commenced.

At the end of the experiment, lesions were visible at the sites of injection. Histological evaluation revealed extensive inflammation of the subcutaneous fat layer extending into the overlying dermis and underlying muscle layers. Tissue necrosis was also observed.

EXAMPLE 18

Treatment of Osteo Arthritis with Mu-Phe-HPhe-O-Ph. $^{45}$Ca$^{2+}$-labelled bones (calvaria) of neonatal mice were maintained in culture. The effect of the test compound on the rate of parathyroid hormone-stimulated $^{45}$Ca$^{2+}$ release was measured over a 24 hour period. An inhibitor of bone resorption (at maximal concentrations) would be expected to inhibit this rate by approximately 70%. The nature of the residual, uninhibitable $^{45}$Ca$^{2+}$-release is not known but could represent chemical exchange of $^{45}$Ca$^{2+}$ with the medium. Mu-Phe-HPhe-O-Ph was dissolved in dimethylsulphoxide which was present in the incubation at concentrations <0.1%.

Mu-Phe-HPhe-O-Ph inhibited resorption in a concentration-related manner. The shape of the inhibition curve appeared to be biphasic in that 50% of the rate of $^{45}$Ca$^{2+}$-release could be inhibited by 1 μm inhibitor whereas at 100 μm an additional 20% was also blocked. IC$_{50}$ values were calculated based upon the initial phase of inhibition.

EXAMPLE 19

Treatment of Osteo Arthritis with Mu-Leu-HPhe-O-Ph. $^{45}$Ca$^{2+}$-labelled bones (calvaria) of neonatal mice were maintained in culture. The effect of the test compound on the rate of parathyroid hormone-stimulated $^{45}$Ca$^{2+}$ release was measured over a 24 hour period. An inhibitor of bone resorption (at maximal concentrations) would be expected to inhibit this rate by approximately 70%. The nature of the residual, uninhibitable $^{45}$Ca$^{2+}$-release is not known but could represent chemical exchange of $^{45}$Ca$^{2+}$ with the medium. Mu-Leu-HPhe-O-Ph was dissolved in dimethylsulphoxide which was present in the incubation at concentrations <0.1%.

Mu-Leu-HPhe-O-Ph inhibited resorption in a concentration-related manner. The shape of the inhibition curve appeared to be biphasic in that 50% of the rate of $^{45}$Ca$^{2+}$-release could be inhibited by 1 μm inhibitor whereas at 100 μm an additional 20% was also blocked. IC$_{50}$ values were calculated based upon the initial phase of inhibition.

EXAMPLE 20

Treatment of Osteo Arthritis with Mu-Tyr(OMe)-HPhe-O-Ph. $^{45}$Ca$^{2+}$-labelled bones (calvaria) of neonatal mice were maintained in culture. The effect of the test compound on the rate of parathyroid hormone-stimulated $^{45}$Ca$^{2+}$ release was measured over a 24 hour period. An inhibitor of bone resorption (at maximal concentrations) would be expected to inhibit this rate by approximately 70%. The nature of the residual, uninhibitable $^{45}$Ca$^{2+}$-release is not known but could represent chemical exchange of $^{45}$Ca$^{2+}$ with the medium. Mu-Tyr(OMe)-HPhe-O-Ph was dissolved in dimethylsulphoxide which was present in the incubation at concentrations <0.1%.

Mu-Tyr(OMe)-HPhe-O-Ph inhibited resorption in a concentration-related manner. The shape of the inhibition curve appeared to be biphasic in that 50% of the rate of $^{45}$Ca$^{2+}$-release could be inhibited by 1 μm inhibitor whereas at 100 μm an additional 20% was also blocked. IC$_{50}$ values were calculated based upon the initial phase of inhibition.

EXAMPLE 21

Treatment of Osteo Arthritis with Z-Phe-Ala-O-Ph. $^{45}$Ca$^{2+}$-labelled bones (calvaria) of neonatal mice were maintained in culture. The effect of the test compound on the rate of parathyroid hormone-stimulated $^{45}$Ca$^{2+}$ release was measured over a 24 hour period. An inhibitor of bone resorption (at maximal concentrations) would be expected to inhibit this rate by approximately 70%. The nature of the residual, uninhibitable $^{45}$Ca$^{2+}$-release is not known but could represent chemical exchange of $^{45}$Ca$^{2+}$ with the medium. Z-Phe-Ala-O-Ph was dissolved in dimethylsulphoxide which was present in the incubation at concentrations <0.1%.

Z-Phe-Ala-O-Ph inhibited resorption in a concentration-related manner. The shape of the inhibition curve appeared to be biphasic in that 50% of the rate of $^{45}Ca^{2+}$-release could be inhibited by 1 μm inhibitor whereas at 100 μm an additional 20% was also blocked. $IC_{50}$ values were calculated based upon the initial phase of inhibition.

EXAMPLE 22

Treatment of Osteo Arthritis with Mu-Tyr(OMe)-HPhe-O-Ph. $^{45}Ca^{2+}$labelled bones (calvaria) of neonatal mice were maintained in culture. The effect of the test compound on the rate of parathyroid hormone-stimulated $^{45}Ca^{2+}$ release was measured over a 24 hour period. An inhibitor of bone resorption (at maximal concentrations) would be expected to inhibit this rate by approximately 70%. The nature of the residual, uninhibitable $^{45}Ca^{2+}$-release is not known but could represent chemical exchange of $^{45}Ca^{2+}$ with the medium. Mu-Tyr(OMe)-HPhe-O-Ph was dissolved in dimethylsulphoxide which was present in the incubation at concentrations <0.1%.

Mu-Tyr(OMe)-HPhe-O-Ph was found to inhibit resorption in mouse calvaria with an $IC_{50}$ of approximately 40 nm. The shape of the inhibition curve was not simple (as was observed with other cysteine protease inhibitors) and the $IC_{50}$ value is for the initial phase of inhibition.

EXAMPLE 23

Treatment of Malaria with Mu-Phe-HPhe-O-Ph. Soluble extracts of *P. falciparum* and *P. vinckei* were prepared and proteolytic activity was assayed with fluorogenic peptide substrate Z-Phe-Arg-AFC. The activity of control samples was compared with activities in the presence of multiple concentrations of Mu-Phe-HPhe-O-Ph. The concentrations at which activity was inhibited by 50% ($IC_{50}$) was calculated.

Mu-Phe-HPhe-O-Ph inhibited the activity of both *P. falciparum* and *P. vinckei*. $IC_{50}$ values of 3.0 nm and 5.1 nm, respectively, obtain.

EXAMPLE 24

Treatment of Malaria with Mu-Leu-HPhe-O-Ph. Soluble extracts of *P. falciparum* and *P. vinckei* were prepared and proteolytic activity was assayed with fluorogenic peptide substrate Z-Phe-Arg-AFC. The activity of control samples was compared with activities in the presence of multiple concentrations of Mu-Leu-HPhe-O-Phe. The concentration at which activity was inhibited by 50%. ($IC_{50}$) was calculated.

Mu-Leu-HPhe-O-Ph inhibited the activity of both P. falciparum and P. vinckei. $IC_{50}$ values of 0.42 nm and 15 nm, respectively, obtain.

EXAMPLE 25

Treatment of Malaria with Mu-Phe-Arg(NO$_2$)-O-Ph. Soluble extracts of *P. falciparum* and *P. vinckei* were prepared and proteolytic activity was assayed with fluorogenic peptide substrate Z-Phe-Arg-AFC. The activity of control samples was compared with activities in the presence of multiple concentrations of Mu-Phe-Arg(NO$_2$)-O-Ph. The concentration at which activity was inhibited by 50% ($IC_{50}$) was calculated.

Mu-Phe-Arg(NO$_2$)-O-Ph inhibited the activity of both P. falciparum and P. vinckei. $IC_{50}$ values of 2.4 nm and 110 nm, respectively, obtain.

EXAMPLE 26

Treatment of Malaria with Mu-Tyr(OCH$_3$)$_2$-HPhe-O-Ph. Soluble extracts of *P. falciparum* and *P. vinckei* were prepared and proteolytic activity was assayed with fluorogenic peptide substrate Z-Phe-Arg-AFC. The activity of control samples as compared with activities in the presence of multiple concentrations of Mu-Tyr(OCH$_3$)$_2$-HPhe-O-Ph. The concentration at which activity was inhibited by 50% ($IC_{50}$) was calculated.

Mu-Tyr(OCH$_3$)$_2$-HPhe-O-Ph inhibited the activity of both *P. falciparum* and *P. vinckei*. $IC_{50}$ values of 8.5 nm and 18 nm, respectively, obtain.

EXAMPLE 27

Treatment of Malaria with Mu-Phe-HPhe-methyl salicylate. Soluble extracts of *P. falciparum* were prepared and proteolytic activity was assayed with fluorogenic peptide substrate Z-Phe-Arg-AFC as described in Rosenthal, Wollish, Palmer and Rasnick, "Antimalarial Effects of Peptide Inhibitors of a *Plasmodium falciparum* Cysteine Proteinase," 88 *J. Clin. Invest.* 1467. The activity of control samples was compared with activities in the presence of multiple concentrations of Mu-Phe-HPhe-methyl salicylate. The concentration at which activity was inhibited by 50% ($IC_{50}$) was calculated.

Mu-Phe-HPhe-methyl salicylate inhibited the activity of P. falciparum. An $IC_{50}$ value of 42 nm obtains.

EXAMPLE 28

Treatment of Gingivitis with Mu-Phe-HPhe-O-Ph. The effect of the inhibitor on gingival inflammation was studied by investigating its ability to prevent the development of experimental gingivitis. Twenty human subjects with healthy gingiva and no periodontal disease were recruited. The subjects received oral hygiene instruction and scaling prior to baseline. The test sites were the mesibuccal crevices on the upper first and second molars and premolars (bicuspids). Acrylic shields were made to cover the gingival margins of these teeth and were worn during oral hygiene to prevent brushing of the test and control sites. During the test period of three weeks the subjects were told to brush only the lower teeth and upper anteriors and to ear the shields during brushing. The left side was used as the test side and the right was the control side in 10 subjects. The sides were reversed in the other 10 subjects so the subjects could act as their own controls. Thirty second GCF samples were taken prior to clinical measurements at baseline and at 1, 2, 3 and 4 weeks. These were assayed for cathepsins B and L-like activities. Clinical measurements of gingival index (GI), gingival bleeding index (GBI) and plaque index (PLI) were taken at test and control sites at zero, one, two, three and four weeks. Following the baseline measurements the inhibitor and placebo were placed at test and control sites and sealed in with Coe-pak for a week. The inhibitor and placebo were coded so that the study was blind.

The GI, GBI and PLI and cysteine proteinase levels were compared at test and control sites. It was observed that the use of Mu-Phe-HPhe-O-Ph reduced all parameters tested at the test sites. Mu-Phe-HPhe-O-Ph can therefore be seen to be effective in treating periodontal diseases such as gingivitis.

The foregoing Examples demonstrate the use of the disclosed proteinase inhibitors to treat specific medical conditions including rheumatoid arthritis, osteo arthritis, malaria and gingivitis are disclosed. The surprising efficacy of the compounds in such in vivo applications could not have been predicted from the prior art, and was determined only after extensive experimentation.

It is understood that a number of variations may be made to adapt the present invention to a particular medical condition without changing the basic compositions and methods disclosed herein. Therefore, while the invention has been illustrated and described in detail in the foregoing Examples, the same are to be considered illustrative and not restrictive in character. It is to be understood that the preferred embodiments have been shown and described, and that all changes and modifications that come within the spirit of the invention are desired to be protected.

We claim:

1. A method of treating medical conditions characterized by extralysosomal cathepsin B, cathepsin L or both comprising therapeutically administering to a medical patient a therapeutically effective amount of a compound of the formula:

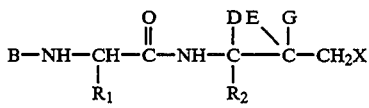

wherein
B is H or an amino acid blocking group for the N-terminal amino acid nitrogen;
$R_1$ is a protected or unprotected α-amino acid side chain on the $P_2$ amino acid radical and is selected such that the $P_2$ amino acid radical is the radical of an α-amino acid selected from the group consisting of unsubstituted and substituted phenylalanine (Ph), leucine (Leu), tyrosine (Tyr) and valine (Val);
$R_2$ is a protected or unprotected α-amino acid side chain on the $P_1$ amino acid radical, and is selected such that the $P_1$ amino acid radical is the radical of an α-amino acid selected from the group consisting of substituted and unsubstituted alanine (Ala), arginine (Arg), aspartic acid (Asp), glutamic acid (Glu), histidine (His), homophenylalanine (HPhe), phenylalanine (Phe), ornithine (Orn), serine (Ser) and threonine (Thr);
X is a fluorine-free leaving group selected from the group consisting of phenoxy, substituted phenoxy and heterophenoxy;
E and G are atoms more electronegative than carbon and bonded to the peptide chain by a double bond when they are the same atom or bonded to the peptide chain by a single bond when each is a separate atom; and
D is hydrogen, methyl or a substituted methyl;
or a pharmaceutical salt thereof.

2. The method of claim 1 wherein said compound is delivered to a medical patient in a pharmaceutically acceptable carrier.

3. A method according to claim 1 wherein said medical condition characterized by activity of extralysosomal cathepsin B, cathepsin L or both is rheumatoid arthritis.

4. A method according to claim 1 wherein said medical condition characterized by activity of extralysosomal cathepsin B, cathepsin L or both is osteo arthritis.

5. A method according to claim 1 wherein said medical condition characterized by activity of extralysosomal cathepsin B, cathepsin L or both is malaria.

6. A method according to claim 1 wherein said medical condition characterized by activity of extralysosomal cathepsin B, cathepsin L or both is a periodontal disease.

7. A method according to claim 1 wherein $R_2$ is an unblocked or blocked side chain on the $P_1$ amino acid radical such that the $P_1$ amino acid radical is the radical of homophenylalanine.

8. A method according to claim 1 wherein B is a 4-morpholinylcarbonyl blocking group.

9. A method according to claim 8 wherein $R_2$ is an unblocked or blocked side chain on the $P_1$ amino acid radical such that the $P_1$ amino acid radical is the radical of homophenylalanine.

10. A method according to claim 8 wherein $R_2$ is an unblocked or blocked heterocyclic analogue of the radical of an α-amino acid selected from the group consisting of alanine (Ala), arginine (Arg), aspartic acid (Asp), glutamic acid (Glu), histidine (His), homophenylalanine (HPhe), phenylalanine (Phe), ornithine (Orn), serine (Ser) and threonine (Thr).

11. A method according to claim 1 wherein X is a fluorine-free leaving group which is also bonded back to $R_2$.

12. A method according to claim 1 wherein D is methyl or a substituted methyl.

13. A method according to claim 1 wherein X is a heterocyclic leaving group.

14. A method according to claim 1, and having a hydrazine replacement for the $P_1$ nitrogen.

15. An inhibitor of cathepsin B, cathepsin L or both, of the formula:

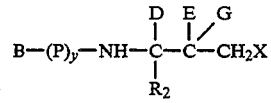

wherein
B is a 4-morpholinylcarbonyl blocking group; each $(P)_y$ is an unprotected or protected α-amino acid radical;
y is a number between zero and three; and
$R_2$ is a side chain on the $P_1$ amino acid radical such that the $P_1$ amino acid radical is the radical of homophenylalanine;
X is a leaving group;
E and G are atoms more electronegative than carbon and bonded to the peptide chain by a double bond when they are the same atom or bonded to the peptide chain by a single bond when each is a separate atom; and
D is hydrogen, methyl or a substituted methyl;
or a pharmaceutical salt thereof.

16. An inhibitor of cathepsin B, cathepsin L or both according to claim 15 wherein X is a fluorine-free leaving group which is also bonded back to $R_2$.

17. An inhibitor of cathepsin B, cathepsin L or both according to claim 15 wherein D is methyl or a substituted methyl.

18. An inhibitor of cathepsin B, cathepsin L or both according to claim 15 wherein X is a heterocyclic leaving group.

19. An inhibitor of cathepsin B, cathepsin L or both according to claim 15, and having a hydrazine replacement for the $P_1$ nitrogen.

20. A method according to claim 1 wherein $R_1$ is Tyr(OMe).

21. A method according to claim 8 wherein $R_2$ is a blocked or unblocked thiazole analogue of the radical of an α-amino acid selected from the group consisting of alanine (Ala), arginine (Arg), aspartic acid (Asp), glutamic acid (Glu), histidine (His), homophenylalanine (HPhe), phenylalanine (Phe), ornithine (Orn), serine (Ser) and threonine (Thr).

22. A method according to claim 8 wherein $R_2$ is a blocked or unblocked amino thiazole analogue of the radical of an α-amino acid selected from the group consisting of alanine (Ala), arginine (Arg), aspartic acid (Asp), glutamic acid (Glu), histidine (His), homophenylalanine (HPhe), phenylalanine (Phe), ornithine (Orn), serine (Ser) and threonine (Thr).

* * * * *